(12) United States Patent
Stotler

(10) Patent No.: US 6,341,295 B1
(45) Date of Patent: Jan. 22, 2002

(54) VIRTUAL REALITY INTEGRATED CALORIC TABULATOR

(76) Inventor: M. Gail Stotler, 621 S. Bellwood, East Alton, IL (US) 62024

( * ) Notice: Subject to any disclaimer, the term of this patent is extended or adjusted under 35 U.S.C. 154(b) by 0 days.

(21) Appl. No.: 09/234,555

(22) Filed: Jan. 20, 1999

Related U.S. Application Data

(60) Provisional application No. 60/072,011, filed on Jan. 21, 1998.

(51) Int. Cl.[7] .................................................. G06F 3/00
(52) U.S. Cl. ...................................................... 708/131
(58) Field of Search ............................... 708/100, 105, 708/131–133

(56) References Cited

U.S. PATENT DOCUMENTS

| | | | |
|---|---|---|---|
| 4,100,401 A | 7/1978 | Tutt et al. ................. | 235/92 T |
| 4,101,071 A | 7/1978 | Brejnik et al. .......... | 235/92 MT |
| 4,159,416 A | 6/1979 | Brejnik et al. .......... | 235/92 MT |
| 4,192,000 A | 3/1980 | Lipsey ....................... | 364/415 |
| 4,212,079 A | 7/1980 | Segar et al. ............... | 364/900 |
| 4,321,674 A | 3/1982 | Krames et al. ........... | 364/413 |
| 4,380,802 A | 4/1983 | Segar et al. ............... | 364/900 |
| 4,885,945 A | 12/1989 | Sakai ..................... | 364/709.02 |
| 4,894,793 A * | 1/1990 | Ikemoto et al. ............. | 708/133 |
| 5,673,691 A | 10/1997 | Abrams et al. ............. | 128/630 |
| 5,691,927 A * | 11/1997 | Gump ......................... | 708/131 |
| 5,704,350 A * | 1/1998 | Williams, III ............. | 708/132 |
| 5,796,640 A * | 8/1998 | Sugarman et al. ........ | 708/132 |
| 5,890,128 A * | 3/1999 | Diaz et al. ................. | 708/100 |
| 6,040,531 A * | 3/2000 | Miller-Kovach et al. ... | 708/133 |
| 6,167,412 A * | 12/2000 | Simons ...................... | 708/105 |

* cited by examiner

Primary Examiner—Tan V. Mai
(74) Attorney, Agent, or Firm—Armstrong Teasdale LLP

(57) ABSTRACT

An improved caloric tabulator that uses virtual reality techniques to give real time feedback to individuals desiring dietary advice and information via a hand held computer.

9 Claims, 2 Drawing Sheets

VIRTUAL REALITY INTEGRATED CALORIC TABULATOR

RELATED APPLICATIONS

The subject application is related to Provisional Patent Application Serial No. 60/072,011 filed Jan. 21, 1998, entitled "Virtual Reality Integrated Caloric Tabulator" (which is hereby incorporated by reference, as if set forth at length.)

BACKGROUND OF THE INVENTION

1. Field of the Invention

This invention relates to apparatus for controlling diets and counting calories.

2. Related Art

Weight control and dietary control are objectives of a substantial portion of the world's population living in developed countries. Adding machines can be used to add up the calories eaten in a given period if one knows the caloric content of the items eaten.

There are many weight control programs and devices. These programs vary from the fad and crash diets to structured nutritional programs that employ trained health professionals to set up individual weight-loss programs and monitor the individual's progress. Similarly, weight loss devices vary from appetite suppression diet pills to computer programs that set up nutritional diets.

Each of these programs and devices has shortcomings. The fad diets offer only short-term weight loss. Structured nutritional programs offer healthy diets, weight goals and encouragement to achieve long-term weight loss, but often fail because the individual is not willing to regularly attend a diet clinic or hospital program. Many of the clinics require the purchase of specialty foods and individuals balk due to the added expense of such foods. Diet pills, like crash diets, at best, provide short-term weight loss without any assurance of a healthy diet. Desktop or computer programs are useful in selecting nutritional diets and counting food calories, but due to the necessity of are cumbersome to use and do not provide the goals and encouragement provided by a diet clinic or hospital program.

Counting the consumption of food calories is a common function of many weight control devices and programs. Existing electronic devices count food calories and perform additional functions.

Other programs purportedly assist the user in identifying those situations that prompt the user to eat. Apparently, the program can point out if the user eats in response to stress, anger or other situations. Presumably, once the user is aware of the situations that provoke eating, the user will know to avoid or not eat because of those situations. Such programs may be termed "behavior awareness programs", rather than the diet and exercise program of the present invention that encourages healthy behaviors and helps the user to establish weight control habits.

In yet another system, that disclosed in U.S. Pat. No. 5,673,691 by Abrams et al. on Oct. 7, 1997 and issued to PICS, Inc., a complex caloric monitor and behavior modification hand held computer system is disclosed which monitors weight, nutrition and exercise and provides visual and audio prompts to tell a user when to eat and exercise and provides suggestions on what to eat, shopping lists and then provides feedback to help motivate the user. This is an overkill approach that is just too complex for most people to follow and much too intrusive. It has not met with significant commercial success.

A better system is needed.

SUMMARY OF THE INVENTION

It is in view of the above problems, particularly with the need for a more user-friendly system to assisting individuals with dietary control, that the present invention was developed. Applicant has rethought the approach dietary calculators and taken a fresh approach that does not require users to remember caloric content of various foods. Being able to view the prior art with great skepticism has enabled the applicant to make a system based on use of an icon based device with easy input similar to that used by virtually all computer users with Windows-based or Apple computers.

It is an object of the invention to provide a simplified system of caloric monitoring using icons for caloric addition items (food intake) and icons for caloric reduction (exercise, etc.).

The invention provides this simplified, and thus more desirable and reliable and less expensive system by which applicant achieves superior results. The invention provides a caloric tabulator comprising a small, food shaped disc body, an LED screen in the body, icons in the screen representing caloric intake/output item, selection buttons for moving between icons on the screen, and timer buttons for stopwatch functions.

Thus in the invention is provided a caloric tabulator system which has a self-contained portable hand-held computer having a processor, memory accessible by the processor, and input keys and a display both in communication with the processor; baseline means for receiving and storing basal metabolism rate (BMR) caloric information regarding a user, including input keys for receiving the BMR information and the memory for storing the BMR information; the processor including a processor adapted to calculate a daily and weekly caloric balance and provide output data including icon representations of input function status, a selected one of the calculated daily or weekly balance, and positive feedback or negative feedback to the display responsive to the value selected balance; and the display being operatively coupled to said processing means and adapted to receive and display the output data.

This simplified, and thus more desirable and reliable and less expensive system by which applicant has achieved a superior result should not be interpreted to mean that more complex caloric tabulator systems are outside the scope of the invention since even the producers of more complex systems may now recognize that conventional wisdom was wrong and use the inventive features described below to reduce the commercial disadvantages of their systems relative to the system described herein.

DESCRIPTION OF THE PREFERRED EMBODIMENTS

Figure 3:
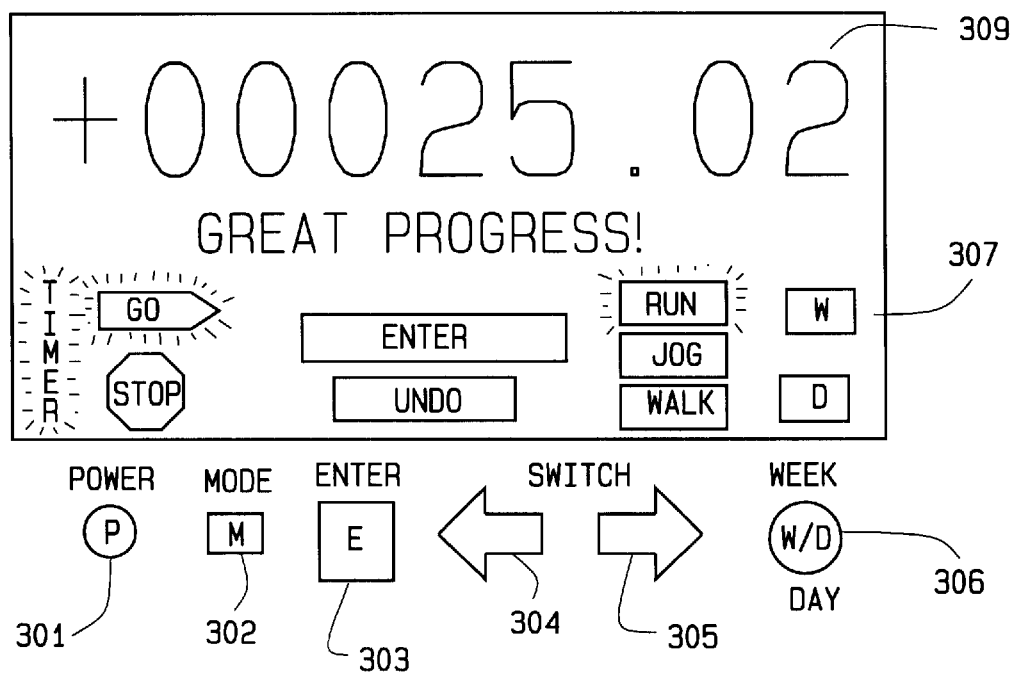

The invention will first be described with reference to FIG. 1 and FIG. 3 which show the face 101 of the body 102 of the hand-held weight control computer 103 of the preferred embodiment and its display 105. This display 105 and a series of buttons 107–112 are on the face of the computer, along with an optional speaker 113, an optional solar cell bank 115 and an apple-shaped exterior. The display 115 is large enough to be read easily by a user, but the body 102 is small enough to be a key fob. The body 102 is small enough to be hand-held or attached to a key chain, in a small purse or small pocket. The buttons on the face of the computer are arranged to be easily reached by the thumbs and other fingers of the user when the computer is held in a user's hand.

Surrounding the display 105 are six control buttons 107–112. Referring to FIG. 3, these buttons are shown aligned along the bottom of the display, although they could be placed at any location such as that shown in FIG. 1. These buttons include the Power button 301 that turns the computer on and off; a Mode button 302 that indexes from one icon to the next in the display; an Enter button 303 that completes a data entry and causes the display to show a following informational screen; a pair of Switch buttons 304, 305 to move between icons and buttons 110; a Week/Day Total button 306 that produces a display of the total cloric balance for the day or for the week. The computer is programmed to provide instant feedback when button 306 is pushed and a negative total is displayed. Since there are only six buttons to use, the device is very user-friendly. The display has suitable icons 307 and a numerical display 309.

Figure 1:
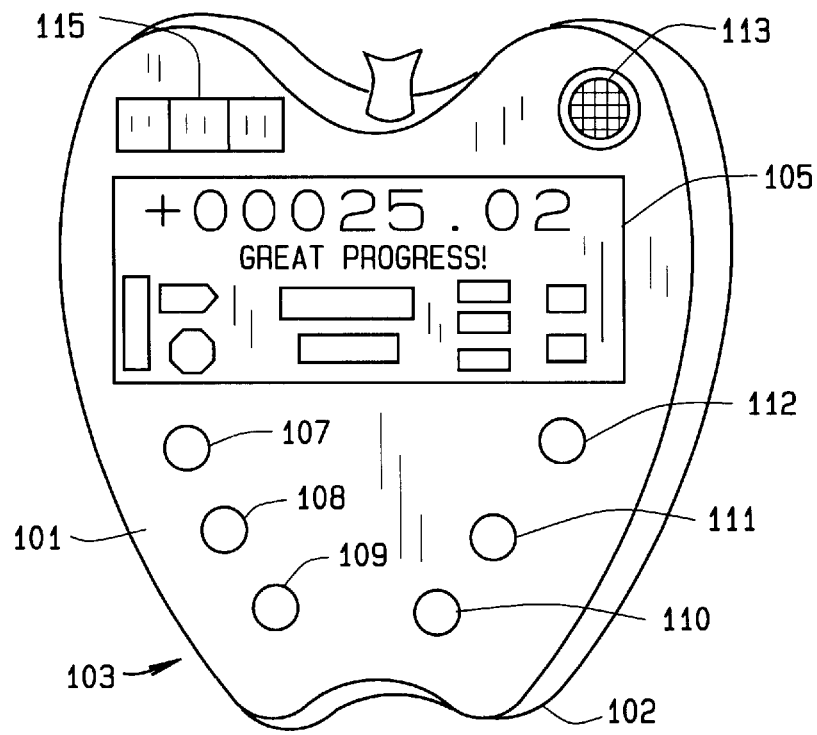
FIG. 1, a front view of a caloric tabulator of the invention.

As seen from FIG. 1, the weight control computer is slim and compact. The computer has a processor, such as an 8-bit processor, that runs the programs that interact with the user. In this computer, all programs interact with the user, with user data entry resulting in immediate feedback to the user. There are no extra programs to present menus on the display, establish goals for the user, prepare progress reports and charts for the user, or other functions which render the computer overly complex. The detailed routines and subroutines that receive the data and provide the feedback are well within the skill of the ordinary artisan as will be readily apparent from a reading of U.S. Pat. No. 5,673,691. This specification therefor omits details of such routine routines, it being understood that a competent hand-held calculator programmer can easily come up with the appropriate routines.

Figure 2:
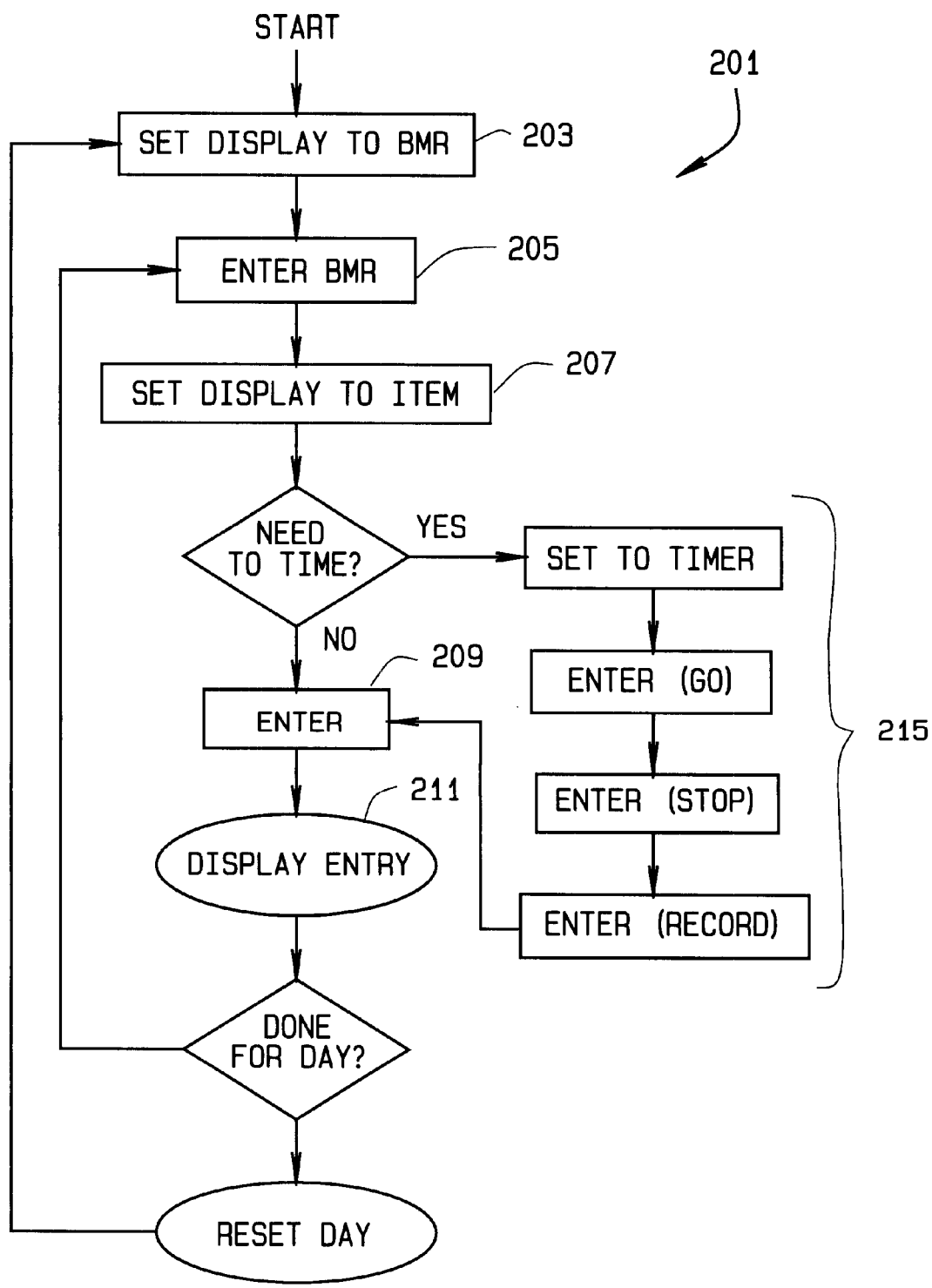
FIG. 2, a flow diagram showing the overall system of the invention in functional terms, and FIG. 3, a front view of a typical LED display.

FIG. 2 shows a block diagram of the software routines that operate within the preferred embodiment of the virtual reality caloric tabulator. In summary, a simplified feedback routine (FBR) 201 interacts with users to help them achieve a particular caloric goal or goals, such as weight and/or diet control. The steps shown in the drawing are self-explanatory and are exemplary. The logic could be varied and sequence could be varied within the scope of the appended claims. The purpose of the FBR is to assist the user both to lose and maintain weight and to develop new behaviors that will help him maintain a healthy weight long-term.

The caloric tabulator uses the above-mentioned FBR 201 as required to help the user achieve his own behavioral goal or goals, as well as developing new behavior that will contribute to his ability to sustain desired results long-term. Many of these routines are well known in the prior art. For example, there are many commercially available routines that set up databases for microprocessor controlled devices or generate messages regarding the date and time. Depending upon the microprocessor controller being used, a person of ordinary skill will be able to set up these routines with no more instruction than provided above. However, for the sake of completeness, further descriptions of some of the routines were briefly given above.

The feedback tabulator is simplified in that the number of input keys is less than nine, and preferably six or four. In the feedback tabulator as shown in FIG. 1, the number of input keys is six. To simplify the operator effort in using the feedback tabulator, it preferably has the input keys provide data entry selected from the group consisting essentially of (icon selection, enter data, undo entry, start time, stop time, request for daily total and request for weekly total.) The feedback tabulator more preferably has the input keys provide data entry selected from the group consisting essentially of (icon selection, enter data, undo entry, stopwatch commands, request for caloric total. The feedback tabulator preferably is less than nine square inches in maximum cross-sectional area and is less than one-half inch thick. The caloric feedback tabulator is preferably less than four square inches in maximum cross-sectional area and is less than one-half inch thick. The feedback tabulator preferably has an exterior shape and color representative of a food item, such as a fruit or vegetable.

While the invention has been described in connection with what is presently considered to be the most practical and preferred embodiment, it is to be understood that the invention is not to be limited to the disclosed embodiment. On the contrary, it is intended to cover various modifications and equivalent arrangements included within the spirit and scope of the appended claims.

The invention will next be described in term of the method of use. As seen in FIG. 2 at step 303, the operator would first index the display to the enter BMR mode by pushing button 302. Then, the operator would enter the caloric limit for the day by pushing button 304 or 305 to move the number up or down. This is entered 205 as a negative number (as a "given" for the basal metabolic rate for maintaining normal ADLs and metabolic cellular processes of the body). Second, each time a food or drink is consumed, the operator would perform steps 207, 209, 211 to enter the caloric intake (a positive number). This entry will be tabulated and then added to the negative initial "BMR" number, throughout the 24-hour period. Third, each time an exercise activity, for the purpose of fitness and/or "burning extra calories" is performed, the tool can (a) calculate 215 the number of calories used (negative number) per minute of activity times the time (minutes) of activity, resulting in the total calorie amount used, and (b) add the resulting negative amount to the initial BMR number, as modified by any preceding activity, throughout the 24 hour period of the day. Fourth, by depressing a button 306 on the front of the disc the operator can view the caloric activity for that 24-hour period. For example,

| | |
|---|---|
| Initial BMR | −1200 |
| Food Item#1 | +0075 |
| Food Item#2 | +0175 |
| Drink Item#1 | +0150 |
| Exercise | −0200 |
| Food/Drink Item | +0800 |
| TOTAL | 0000 |

Fifth, by depressing another button, or the same button 306 twice, the operator may have the total for the week. Finally, the tool will recognize the various entry types and respond with positive or negative reinforcement. For example, for negative daily or weekly totals, the device would respond with bells and whistles or other positive indicator. For zero totals, the system would respond with praise and encouragement. For plus totals, the system would produce reminders and warnings.

In view of the foregoing, it will be seen that the stated objects of the invention are achieved. The above description explains the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description shall be interpreted as illustrative rather than limiting. Thus, the breadth and scope of the present invention should not be limited by any of the above-described exemplary embodiments, but should be defined only in accordance with the following claims appended hereto and their equivalents.

The patents referenced herein are incorporated in their entirety for purposes of background information and additional enablemen.

What is claimed is:

1. A caloric tabulator system, comprising:

a self-contained portable hand-held computer having a processor, memory accessible by the processor, and input keys and a display both in communication with the processor;

baseline means for receiving and storing basal metabolism rate (BMR) caloric information regarding a user, including the input keys for receiving the BMR information and the memory for storing the BMR Information;

the processor configured to calculate a daily and weekly caloric balance and provide output data including icon representations for caloric addition items, caloric subtraction items, a selected one of the calculated daily or weekly balance, and positive feedback or negative feedback to the display responsive to the value selected balance;

the display being operatively coupled to said processing means and adapted to receive and display the output data, including the icon representations; and the input keys configured to allow a user to select among the icon representations for at least one of caloric addition items, caloric subtraction items, calculated balances and feedback.

2. The feedback tabulator of claim 1, wherein the number of input keys is less than nine.

3. The feedback tabulator of claim 1, wherein the number of input keys is six.

4. The feedback tabulator of claim 1, wherein the input keys provide data entry selected from the group consisting essentially of icon selection, enter data, undo entry, start time, stop time, request for daily total and request for weekly total.

5. The feedback tabulator of claim 1, wherein the input keys provide data entry selected from the group consisting essentially of icon selection, enter data, undo entry, stopwatch commands, request for caloric total.

6. The feedback tabulator of claim 1, wherein the caloric tabulator is less than nine square inches in maximum cross-sectional area and is less than one-half inch thick.

7. The feedback tabulator of claim 6, wherein the caloric tabulator is less than four square inches in maximum cross-sectional area and is less than one-half inch thick.

8. The feedback tabulator of claim 6, wherein the tabulator has an exterior shape and color representative of a food item.

9. The feedback tabulator of claim 7, wherein the exterior shape is of a fruit or vegetable.

* * * * *